United States Patent [19]
Chiabrera et al.

[11] Patent Number: 5,917,877
[45] Date of Patent: Jun. 29, 1999

[54] PLAIN X-RAY BONE DENSITOMETRY APPARATUS AND METHOD

[75] Inventors: Alessandro Chiabrera, Genoa, Italy; Robert S. Siffert, New York; Jonathan J. Kaufman, Brooklyn, both of N.Y.

[73] Assignee: Cyberlogic, Inc., New York, N.Y.

[21] Appl. No.: 08/924,154

[22] Filed: Sep. 5, 1997

[51] Int. Cl.⁶ .................................. G01N 23/04
[52] U.S. Cl. .............................. 378/5.3; 378/207
[58] Field of Search ........................... 378/51, 53, 54, 378/56, 58, 207

[56] References Cited

U.S. PATENT DOCUMENTS

| | | | |
|---|---|---|---|
| 3,847,141 | 11/1974 | Hoop | 128/2 |
| 3,848,130 | 11/1974 | Macovski | 250/369 |
| 3,996,471 | 12/1976 | Fletcher et al. | 250/444 |
| 4,029,963 | 6/1977 | Alvarez et al. | 250/360 |
| 4,513,078 | 4/1985 | Sandrik, et al. | 430/496 |
| 4,603,428 | 7/1986 | Sandrik et al. | 378/174 |
| 4,754,763 | 7/1988 | Doemland | 128/739 |
| 4,811,373 | 3/1989 | Stein | 378/54 |
| 5,070,248 | 12/1991 | Pesce | 250/483.1 |
| 5,122,664 | 6/1992 | Ito et al. | 378/207 X |
| 5,187,731 | 2/1993 | Shimura | 378/207 |
| 5,259,384 | 11/1993 | Kaufman et al. | 128/660.01 |
| 5,368,044 | 11/1994 | Cain et al. | 128/739 |
| 5,426,709 | 6/1995 | Yoshida et al. | 382/132 |
| 5,651,363 | 7/1997 | Kaufman et al. | 128/660.2 |
| 5,687,210 | 11/1997 | Maitrejean et al. | 378/56 X |

OTHER PUBLICATIONS

Cosman, F., et al., "Radiographic Absorpitometry: A Simple Method for Determination of Bone Mass", Osteoporosis Int. (1991) 2:34–38. no month.

*Primary Examiner*—David P. Porta
*Attorney, Agent, or Firm*—Dykema Gossett PLLC

[57] ABSTRACT

Non-invasive quantitative plain radiographic evaluation of bone in a bony locale of a body is performed by subjecting the bony locale to a broadband collimated x-ray beam having energy in the range of about 20 keV to 150 keV. Alongside the bony locale is a multiple-material phantom containing at least two distinct materials. An energy-selective multiple-film detector cassette containing at least two films is placed under the body and multiple-material phantom to receive the transmitted x-ray beam. The films in the cassette are developed and digitally scanned to produce sets of multiple-material phantom data and sets of bone data. The data sets are then processed with a nonlinear algorithm whereby to generate the indicated estimate of bone status, namely, bone-mineral density.

4 Claims, 4 Drawing Sheets

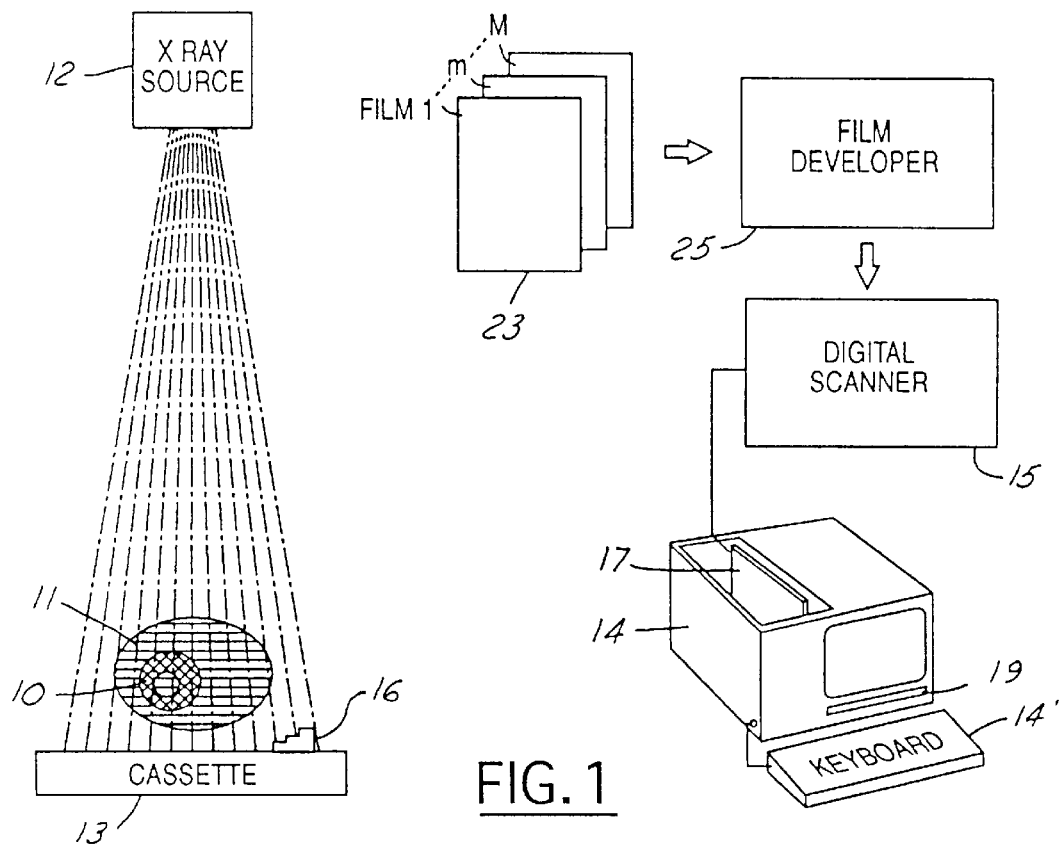
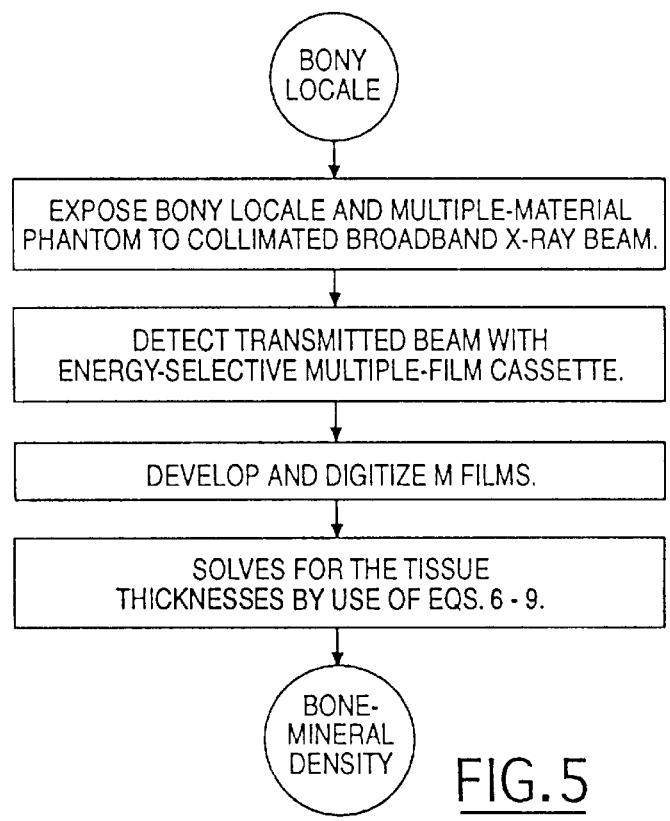
FIG. 1
FIG. 5

PLAIN X-RAY BONE DENSITOMETRY APPARATUS AND METHOD

BACKGROUND OF THE INVENTION

The invention pertains to apparatus and method for non-invasively and quantitatively evaluating bone-mineral density in vivo at a given time, where the bone-mineral density is characterized in terms of mineral content (i.e., grams of bone) or in terms of areal mineral density (i.e., grams of bone per square centimeter).

In recent years, various attempts have been made to use diverse forms of energy to assess the condition of bone tissue in vivo. The primary means utilized presently has involved the application of ionizing radiation, namely x-rays. These x-ray based methods are either extremely simplistic, which provide inaccurate and imprecise estimates of bone mineral density, or very expensive. Although providing reasonably precise and accurate estimates of bone mineral density, these high cost methods makes their widespread use problematic. This is especially true given the constraints on health care financing.

Apparatuses which utilize ionizing electromagnetic radiation are well known. A review of these radiation based methods may be found in the article by Ott et al., in the *Journal of Bone and Mineral Research*, Vol. 2, pp. 201–210, 1987. These techniques all operate on the basic principle that the attenuation of an x-ray beam depends on the amount of bone present at a particular anatomical site in a subject's body, and that this attenuation (and therefore some information on the amount of bone present) can be evaluated. Several techniques exist for performing this type of densitometric measurement, such as single photon absorptiometry (SPA), dual photon absortiometry (DPA), single energy x-ray absortiometry (SXA), dual energy x-ray absorptiometry (DXA), and quantitative computed tomography (QCT). A related but simpler bone density estimation method, known as radiographic densitometry (RA), has also been described (see, for example the 1991 publication by F. Cosman, B. Herrington, S. Himmelstein and R. Lindsay entitled "Radiographic Absorptiometry: A Simple Method for Determination of Bone Mass," in *Osteoporosis International, Volume* 2, pp. 34–38. This technique, based on a plain radiograph, is applicable to appendicular sites only; it has mostly been applied to evaluation of the bone mineral density of the phalanges (fingers). It utilizes digital image processing to process a plain radiograph which was obtained with an aluminum alloy reference step wedge placed adjacent to the hand. Unfortunately, this technique is affected by varying amounts of soft tissue, as well as the variability of x-ray energy source spectra associated with different machines. The broad spectrum of conventional x-ray equipment implies also a phenomenon known as beam hardening. Beam hardening is the change in energy spectrum that occurs as the x-ray beam traverses the interrogated object due to the energy-dependencies of the attenuations of the materials within the object, and can have a significant effect on accuracy associated with bone mineral density estimates.

Other x-ray based techniques for bone assessment have also been described previously. These methods may be based on the evaluation of various geometric features of bone from an x-ray image. These features can include, for example, cortical bone thickness and hip axis length; these measurements are not directly related to the bone mineral density quantity described above.

Acoustic techniques have also been utilized for non-invasive bone assessment, including for example, both ultrasonic and low-frequency vibrational methods. Although these techniques have the potential for providing a great deal of information on bone density and strength, they have not yet become widely used for in vivo bone assessment. Some reasons for this are that the techniques are highly sensitive to positioning and coupling of the acoustic transducers and are also affected by soft tissue overlying the bone.

Yoshida, et al., U.S. Pat. No. 5,426,709 discloses a plain x-ray measurement method and apparatus for evaluating bone mineral density of a bone, upon determination of quantity level of light that transmits through the x-ray film. The Yoshida, et al. device adjusts the light intensity level so that it is within a predetermined quantity range of light, in comparison to that which is transmitted through an aluminum step wedge. A temperature compensation for an output from the transmitting light detecting unit, i.e., a charge coupled device image sensor, is carried out by utilizing a light shielded output from the sensor.

U.S. Pat. No. 4,811,373 to Stein discloses a device to measure bone density. In the invention, Stein describes an x-ray tube operating at two voltages to generate a pencil beam, together with an integrating detector. The detector measures the patient-attenuated beam at the two energy levels (known commonly as dual energy x-ray absorptiometry) of the pencil beam. Calibration is accomplished by a digital computer on the basis of passing the pencil beam through a known bone-representing substance as the densitometer scans portion of the patient having bone and adjacent portions having only flesh.

Fletcher et al., in U.S. Pat. No. 3,996,471, disclose another dual energy x-ray absorptiometry method. In this invention, a target section of a living human body is irradiated with a beam of penetrative radiations of preselected energy to determine the attenuation of such beam with respect to the intensity of each of two radiations of different predetermined energy levels. The resulting measurements are then employed to determine bone mineral content.

Alvarez et al., in U.S. Pat. No. 4,029,963, disclose a method for decomposing an x-ray image into atomic-number-dependent and density-dependent projection information. The disclosed technique is based on the acquisition of x-ray images from the low and high energy regions, respectively.

Kaufman et al., U.S. Pat. Nos. 5,259,384 and 5,651,363, disclose method and apparatus for ultrasonically assessing bone tissue. In the first of the two Patents, a composite sine wave acoustic signal consisting of plural discrete frequencies within the ultrasonic frequency range to 2 MHz are used to obtain high signal-to-noise ratio of the experimental data. A polynomial regression of the frequency-dependent attenuation and group velocity is carried out, and a non-linear estimation scheme is applied in an attempt to estimate the density, strength, and fracture risk of bone in vivo. In the second of the two Patents, a parametric modeling approach is used in a comparative analysis for assessment of bone properties.

U.S. Pat. No. 3,847,141 to Hoop discloses a device to measure bone density as a means of monitoring calcium content of the involved bone. A pair of opposed ultrasonic transducers is applied to opposite sides of a patient's finger, such that recurrent pulses transmitted via one transducer are "focused" on the bone, while the receiving response of the other transducer is similarly "focused" to receive pulses that have been transmitted through the bone. The circuitry is arranged such that filtered reception of one pulse triggers the next pulse transmission; the filtering is by way of a bandpass filter, passing components of received signals, only in the 25 to 125 kHz range; and the observed frequency of retriggering is said to be proportional to the calcium content of the bone.

Doemland, U.S. Pat. No. 4,754,763 discloses a noninvasive system for testing the integrity of a bone in vivo. He uses low-frequency mechanical vibrations to characterize the state of healing in a fractured bone. The frequency response is used to classify the stage of healing.

Cain et al., U.S. Pat. No. 5,368,044 applied a similar method, namely, low-frequency mechanical vibrations, to assess the state or stiffness of bone in vivo. The method evaluates the peak frequency response or a cross-correlation of the frequency vs. amplitude response.

The prior art, exemplified by the references that have been briefly discussed, have had little success in providing a simple, relatively inexpensive device or method for accurate quantitative clinical non-invasive assessment of bone. They have focussed primarily on expensive x-ray bone densitometric techniques, such as dual energy methods, or much more inexpensive plain radiographic absortiometry methods. These latter plain x-ray methods unfortunately suffer at present from relatively low accuracy and precision, inability to accurately measure bone-mineral density at arbitrary anatomical sites, errors due to variability in thickness of overlying soft tissue, and the confounding effects of variations in x-ray machines and associated settings. On the other hand, acoustic (low-frequency vibrational or ultrasonic) means have not yet produced an accurate practical method for clinical bone assessment either.

Of great utility in the field of bone densitometry would be a technique as simple, inexpensive and easy to implement as plain radiographic absorptiometry, while offering also the enhanced accuracy and precision of current (but expensive) x-ray bone densitometers, such as by dual energy x-ray absorptiometry.

BRIEF STATEMENT OF THE INVENTION

It is accordingly an object of the invention to provide an improved method and apparatus for non-invasive and quantitative evaluation of bone tissue in vivo.

Another object is to meet the above object, such that bone-mineral density may be readily and more reliably quantitatively evaluated than heretofore.

A specific object is to achieve the above objects in such a way that an estimate of bone mineral density can be obtained that it is largely insensitive to the confounding effects of soft tissue.

A specific object is to achieve the above objects in such a way that an estimate of bone mineral density can be obtained that it is largely insensitive to the confounding effects due to variations in plain x-ray equipment.

A specific object is to achieve the above objects substantially with conventional and widely available plain radiographic x-ray equipment.

Briefly stated, the invention in its presently preferred form achieves the foregoing objects by subjecting a bony locale of a body to a collimated x-ray beam, generated by a conventional plain x-ray radiography machine. The x-ray beam as utilized contains energy in a relatively broadband region, from about 20 keV to about 150 keV. Adjacent to the bony portion of the body and exposed simultaneously to the x-ray beam is a multiple-material phantom. The phantom is comprised of K distinct materials, whose linear attenuation coefficients are also distinct. The phantom has associated with it a set of distinct thicknesses for each material component and spatial location on the phantom itself, which are assumed to be known a priori. The broadband x-ray beam, after propagation through either a body portion or the multiple-material phantom, is received by a multiple-film detector cassette containing multiple films and scintillation screens, all arranged parallel to one another. The multiple-film cassette is configured to expose M ($\leq$K) individual films which have received different relative portions of the x-ray source energy spectrum. The exposure of the M films to distinct x-ray energy spectrums is achieved through the use of M-1 sheet filters placed between each of the films in the multiple-film cassette, starting after the first film. In this arrangement, the first film (closest in distance to the interrogated body portion) receives x-ray energy which did not propagate through any of the M-1 filter sheets, whereas the last (i.e., the $M^{th}$, furthest in distance from the interrogated body portion) receives x-ray energy which propagated through all of the M-1 filter sheets. The multiple-film cassette, which may also be referred to herein as an energy-selective multiple-film cassette, includes also scintillating screens placed adjacent to each of the M films, which are used to expose the films to visible light photons, respectively, in order to produce appropriately exposed M films. The M films are then developed according to conventional methods, and subsequently digitally scanned to obtain M gray-level intensity radiographic images associated with the M films. The M radiographic images are each comprised of a set of gray-level intensity data values associated to each picture point corresponding to the bony locale of the body and a set of gray-level intensity data values associated to each picture point corresponding to the multiple-material phantom. The two data sets of gray-level intensities, namely, the data set of gray-level intensity values corresponding to the bony portion of the body and the data set of gray-level intensity values corresponding to the multiple-material phantom, associated with each of the M images, are then used as input to a numerical algorithm to generate the indicated estimate of the status of bone that is being analyzed, namely, to obtain an accurate and precise estimate of the associated bone-mineral density, as given by the areal bone density (in grams per square centimeter).

BRIEF DESCRIPTION OF THE DRAWINGS

The invention will be described in detail for a presently preferred embodiment, in conjunction with the accompanying drawings, in which:

FIG. 1 is a schematic diagram showing the interconnected relation of components of apparatus of the invention.

FIG. 5 is a flow chart of computer-controlled operations associated with FIG. 1, in automatically analyzing and quantitatively reporting an estimate of bone mineral density.

DETAILED DESCRIPTION OF THE INVENTION

The invention will be described in detail for a presently preferred embodiment, in conjunction with the accompanying drawings.

The invention is shown in FIG. 1 in application to interconnected components for constructing apparatus for performing methods of the invention, namely, for non-invasively and quantitatively evaluating the bone mineral density of bone tissue in viva at a given time. Some of these components are commercially available from different sources and will be identified before providing detailed description of their total operation. Other components in FIG. 1 are not commercially available and need to be fabricated using known and currently available technology.

Figure 2:
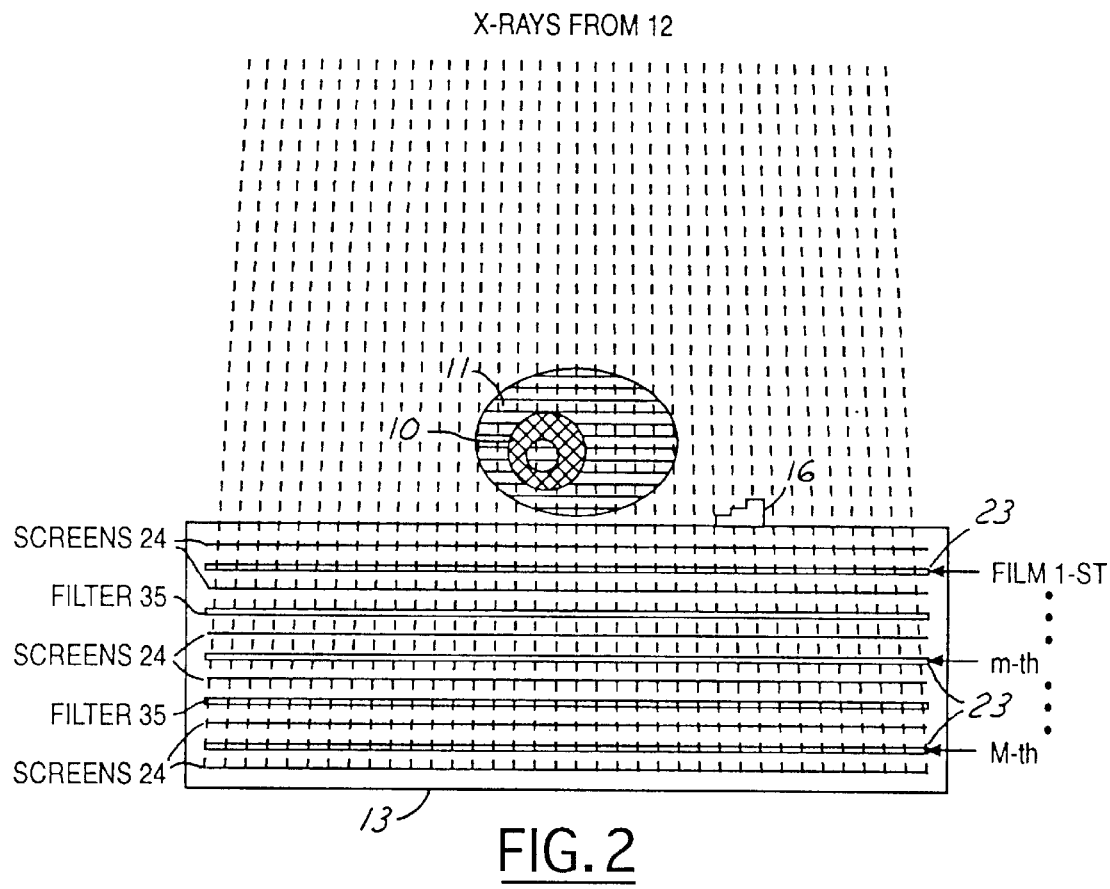
FIG. 2 is a schematic diagram showing the multiple-film detector cassette used in one embodiment of the invention which is a modified version of a commercially available x-ray detector cassette.
Figure 3:
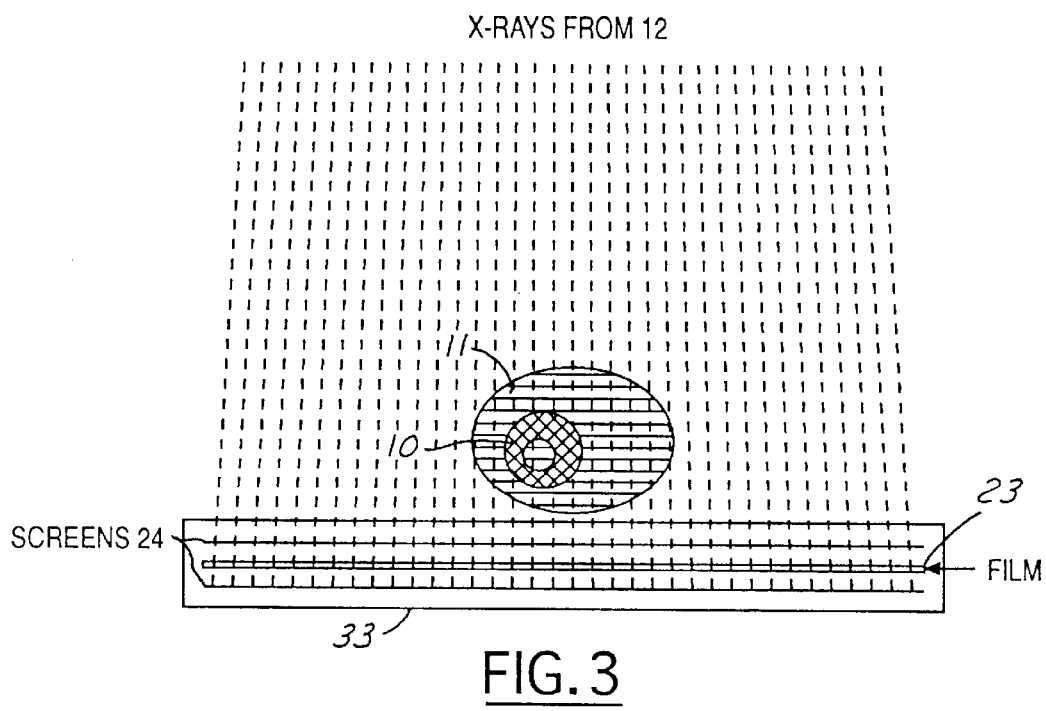
FIG. 3 is a schematic diagram showing a standard double-screen film cassette which in a modified form is used in the presently preferred embodiment of FIG. 2.
Figure 4:
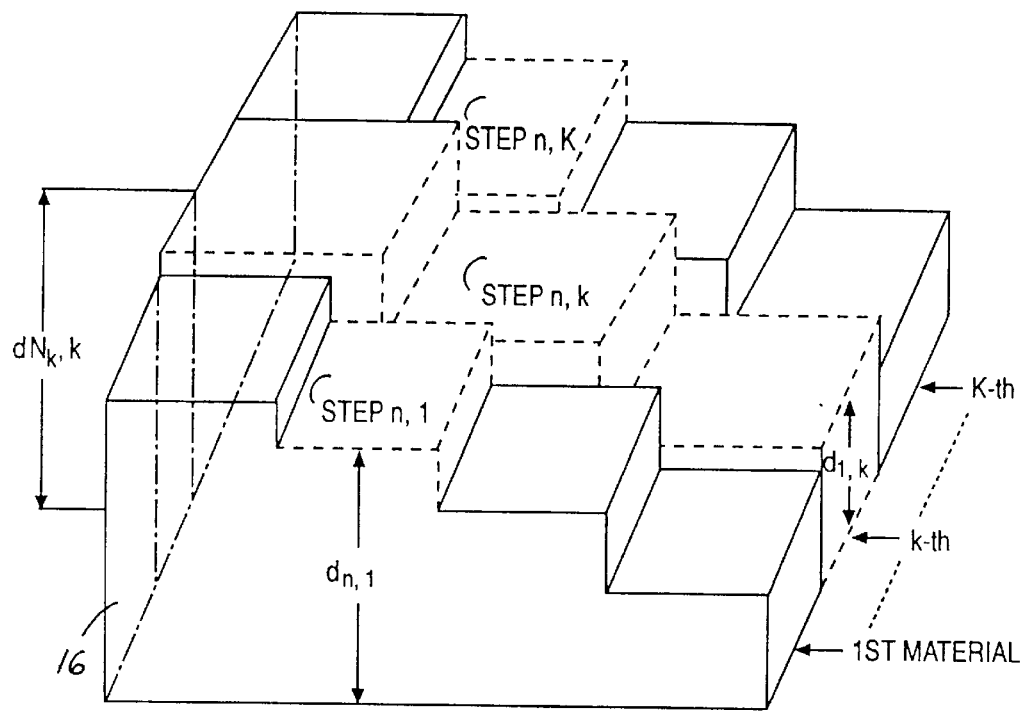
FIG. 4 is a schematic diagram showing the multiple-material phantom.

In FIG. 1, the bone 10 to be analyzed in a bony locale of a body is shown surrounded by soft tissue 11 and to be interposed between an x-ray radiographic source 12 and a multiple-film detector cassette 13. The x-ray radiographic source may be any of a large number of such sources, and may suitably be Model MTX 360 Generator, available from Picker International Corporation of Cleveland, Ohio; Model MTX may suitably be part of a Clinix VPE System, available from the same company, Picker International. As shown, x-ray source 12 is used to generate a collimated x-ray beam of relatively broadband energy which propagates through the bone 10 and its surrounding soft tissue 11. Detector cassette 13 is a modified version of a standard commercial double-screen film cassette, which may suitably be a Quanta Rapid cassette available from Stirling Diagnostic Imaging of Newark, Del. With additional reference to FIG. 2, it may be seen that the height of the case of multiple-film cassette 13 has been mechanically adapted to be of increased size, in comparison to the standard double-screen film cassette, shown in FIG. 3 as 33. Also shown are a set of M double-sided emulsion radiographic films 23, each film being sandwiched between a pair of scintillating screens 24. The film may suitably be OTG Radiology film, available from Stirling Diagnostic Imaging of Newark, Del.; any standard radiology film may be used. The scintillating screens are included in the Quanta Rapid cassette, produced by Stirling Diagnostic Imaging as well. Also shown in FIG. 2 are a set of M-1 thin metal plates or filters 35, which are located alternately between each of the M film 23 and screen 24 sandwiches. The filters 35, also known as half-value layer attenuators, may be suitably Model No. 07-430EY, available from Nuclear Associates of Carle Place, N.Y. All the films, screens and filters in the multiple-film cassette are in tight contact. With reference again to FIG. 1, a multiple-material phantom 16 is shown placed adjacent to the soft tissue 11, and on top of the detector cassette 13, facing towards the side which is nearest the x-ray source 12. With additional reference to FIG. 4, the multiple-material phantom 16 is shown as a set of K step-wedges, each step-wedge being comprised of a distinct material, and each material k, where k=1, . . . , K, arranged in a staircase pattern of $N_k$ steps. The multiple-material phantom may be constructed from a wide variety of available materials, including solids, such as aluminum and copper alloys, plastics, calcium compounds such as calcium-hydroxyapatite, as well as liquids, such as water and bi-potassium-phosphate solutions.

With reference again to FIG. 1, basic operation is governed by computer means 14, which may be a PC computer, such as the "GP6-266" available from Gateway 2000, Inc., North Sioux City, S. Dak.; as its designation suggests, this computer contains a 266 MHz clock-pulse generator, and an Intel Pentium II processor, with provision for keyboard instruction at 14'.

Also shown in FIG. 1 is a film developer 25, which is used to develop the films 33 exposed in the multiple-film cassette 13. The film developer 25 is available from a wide number of sources; most suitably the Model Xomat M6B available from Kodak of Rochester, N.Y., may be used.

A digital scanner 15 is also shown and is relied upon to produce a digitized image from the optical density of each developed film (i.e., radiograph). The scanner may suitably be a MicroTek ScanMaker IIHR with a transparency adaptor MicroTek Model No. SM II TPO, available from MicroTek Lab., Inc., of Redondo Beach, Calif. The scanner is able to digitize an entire x-ray in a matter of seconds, producing literally millions of digitized image points. The scanner is interfaced to the personal computer 14, which allows for the transfer to the computer of all the digitized image data via computer interface 17 for processing, storage and display.

Finally, general signal-processing/display/storage software, for the signal-processing/image-processing control and operation of the computer is not shown but will be understood to be a floppy disk loaded at 19 into the computer; this software is suitably the MATLAB for Windows, available from The Math Works, Inc., Natick, Mass. This software includes the Image Processing, Optimization and Signal Processing Toolboxes. Further software, also not shown but loaded into the computer, is least-squares regression modeling software, identified as TableCurve, a product of Jandel Scientific, Inc., San Rafael, Calif., a Fortran language compiler and a Visual C++ language compiler, both available from Microsoft Corporation, Beaverton, Oreg. In the presently preferred embodiment, involving the described components of FIG. 1, the computer will be understood to be further programmed to generate an estimate of the above-indicated and currently analyzed bone property, namely, areal bone-mineral density.

In the presently preferred embodiment of the invention and with additional reference to the flow diagram of FIG. 5, a bone 10 and its surrounding soft tissue 11 are subjected to a collimated x-ray beam from source 12. Adjacent and alongside to the bone 10 and surrounding soft tissue 11 is the multiple-material phantom 16, which also is subjected to the collimated x-ray beam from source 12. The energy-selective multiple-film cassette is positioned under both the bone 10 with its surrounding soft tissue 11, as well as multiple-material phantom 16. The M films in the multiple-film cassette, in which each receive a relatively different portion of the energy spectrum of the x-ray beam, are then developed by the film developed 25, and digitized using scanner 15. The M digitized images are then transferred to computer 14 via the computer interface 17.

In the presently preferred embodiment of the invention, the multiple-material phantom 16 is comprised of K=2 materials, aluminum and polymethylmethacrylate (PMMA), and both portions of the multiple-material phantom are arranged in a staircase shape. The aluminum portion of the phantom has a step size (height) of 1 mm, an initial step height of 0.5 mm, and a total of 20 steps. The plastic portion of the phantom has a step size of 2 mm, an initial step height of 1 mm, and a total of 20 steps as well. The notation adopted for the thickness of the multiple-material phantom is as follows. Let $d_{n,k}$, n=1, . . . , $N_k$, k=1, . . . , K denote the thickness of the $k^{th}$ material at the $n^{th}$ step in the multiple-material phantom, and $N_k$, k=1, . . . , K denote the number of steps in the kth material. It should be understood in general that the shape of the phantom need not necessarily be of a staircase shape; rather, any shape that provides for distinct thicknesses may be used. It should further be understood that the multiple-material phantom can further serve for the purposes of size calibration, that is, the scaling of the radiographic images in terms of actual physical dimensions. For this purpose, it may be useful to include calibration marks on the phantom. Such dimension normalization techniques are well-known in the art.

In the presently preferred embodiment, let $H_{m,n,k}$ denote the exposure of film m, at the points associated with the $n^{th}$ step of the $k^{th}$ material of the multiple-material phantom 31. Then $H_{m,n,k}$ may be expressed as:

$$H_{m,n,k} = \int_{E_1}^{E_2} f_m(E) g_{n,k}^P(E) dE \qquad (1)$$

where $$g_{n,k}^P(E) = e^{-d_{n,k} \mu_k^P(E)} \qquad (2)$$

Figure 6:
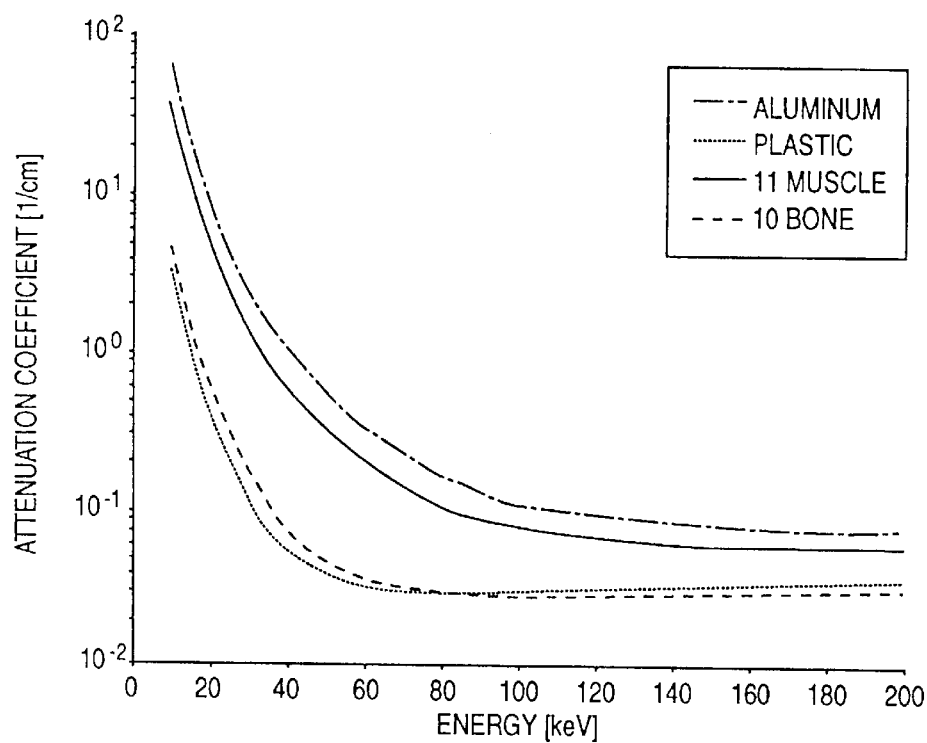
FIG. 6 is a graph showing linear attenuation coefficients for several materials of standardized density.

In Eq. 2, $\mu_k^P(E)$ is the linear attenuation coefficient at energy E of material k in the multiple-material phantom, and $E_1$ and $E_2$ are lower and upper bounds for the x-ray beam energy spectrum. In the presently preferred embodiment, $E_1$=20 keV, $E_2$=150 keV, and the linear attenuation coefficients are assumed to be known a priori. As is well known in the art, values for these coefficients may be obtained by straightforward measurement or looked up in the radiological physics literature. An excellent reference for this is the book by Frank H. Attix entitled *Introduction to Radiological Physics and Radiation Dosimetry*, published by Wiley Interscience in New York in 1986, which is incorporated by reference hereinto. For example, Appendix D3 of this reference provides an extensive set of attenuation data for a wide range of materials, including aluminum and plastics. Some attenuation curves based on the data in this Appendix D3 are shown in FIG. 6.

In Eq. 1, $f_m(E)$ is a weighting function which accounts for effects associated with exposure of film m in the multiple-film cassette, apart from the effects of the phantom itself. Thus, in particular, $f_m(E)$ includes the effects of the energy spectrum of the x-ray source (which in general varies from machine to machine), the effects of the scintillating screens, as well as the effects of the sheet filters. The weighting function can also include some effects of film development, as discussed infra. In the presently preferred embodiment, the exposure of the $m^{th}$ film is affected by the preceding m-1 sheet filters. It should be understood that $f_m(E)$, m=1, ..., M, are unknown functions which need to be identified.

Next, let $T_m$ denote the exposure of film m, at the point associated with film image m, at a point located within the bony locale. Then $T_m$ may be expressed as $$T_m = \int_{E_1}^{E_2} f_m(E) g(E; d_l) dE \qquad (3)$$

where $g(E; d_l)$ is given by $$g(E; d_l) = e^{-\sum_{k=1}^{K} \sum_{l=1}^{L} b_{kl} d_l \mu_k^P(E)} \qquad (4)$$

In Eq. 4, d=1, ..., L are unknown thicknesses of L tissues at the bony locale. In the presently preferred embodiment, there are assumed to be only two (L=2) tissues present, i.e., bone tissue (=1) and soft tissue (=2), respectively, at a point in the bony locale. It should be understood and appreciated that $d_1$ is related to the bone-mineral density value of clinical interest, known as areal-BMD, expressed in units of g cm$^{-2}$.

It is obtained by multiplying the bone tissue thickness $d_1$, (determined using the methods of the present invention) by the assumed standard volumetric density, $\rho_1$, of bone tissue, i.e., areal-BMD=$d_1 \cdot \rho_1$ [g cm$^{-2}$]. In the presently preferred embodiment, $\rho_1$=1.85 g cm$^{-3}$, which is also the value given by the International Commission on Radiological Protection (ICRP), as noted in Appendix B2 and B3 of the book by Attix referred to supra. It should similarly be understood that another variable of clinical interest, the bone mass, m, in grams, may also be determined by a simple numerical scaling operation. It can be obtained by multiplying the areal-BMD by the area, A, of the region over which the areal-BMD was determined, i.e., m=areal-BMD · A. It should be further understood that similar scaling procedures can be applied to any tissue or other material whose respective thicknesses may be determined according to the methods disclosed herein.

The coefficients $b_{kl}$ are determined from the equation $$\mu_l(E) = \sum_{k=1}^{K} b_{kl} \mu_k^P(E), l = 1, ..., L \qquad (5)$$

Eq. 5 is based on the fact that a linear attenuation coefficient may be decomposed into a finite set of independent contributions from specific modes of photon interactions (see for example, the book by A. Macovski entitled *Medical Imaging Systems*, 1983, Prentice-Hall, N.J.) It is thus to be understood that any attenuation function can be expressed as a linear combination of a set of other attenuation functions, as in Eq. 5 above. In general, a maximum of four (4) distinct attenuation functions are sufficient to represent any other attenuation function. In the presently preferred embodiment, two (K=2) attenuation functions associated with two materials (i.e., aluminum and PMMA) are used. In Eq. 5, $\mu(E)$, =1, ..., L are the linear attenuation coefficients for the L tissues, respectively, whose values are also assumed to be known a priori (see for example, FIG. 6 for the attenuation curves for bone 10 and muscle 11). They may be obtained in the same fashion as described supra for the multiple-material phantom coefficients $\mu_k^P(E)$. It is then straightforward to solve Eq. 5 for $b_{kl}$, by substituting in the known values for the attenuation coefficients $\mu(E)$ and $\mu_k^P(E)$. Eq. 5 represents a set of linear equations and can be solved with a variety of computer software packages; in the presently preferred embodiment, MATLAB offers an optimal environment in which to obtain the solution of Eq. 5.

In solving for the unknown tissue thicknesses, it should be understood that it is necessary to express the exposure variables $H_{m,n,k}$ and $T_m$ in terms of the variables actually measured, namely, the image pixel values associated with the multiple-material phantom and the bony locale, respectively. Denoting the former by $I_{m,n,k}$ and the latter by $I_m$, the relationships between the variables are given by $$H_{m,n,k} = \left[\frac{I_{0,m}}{I_{m,n,k}}\right]^{\frac{1}{\gamma}} \qquad (6)$$

$$T_m = \left[\frac{I_{0,m}}{I_m}\right]^{\frac{1}{\gamma}} \qquad (7)$$

Figure 7:
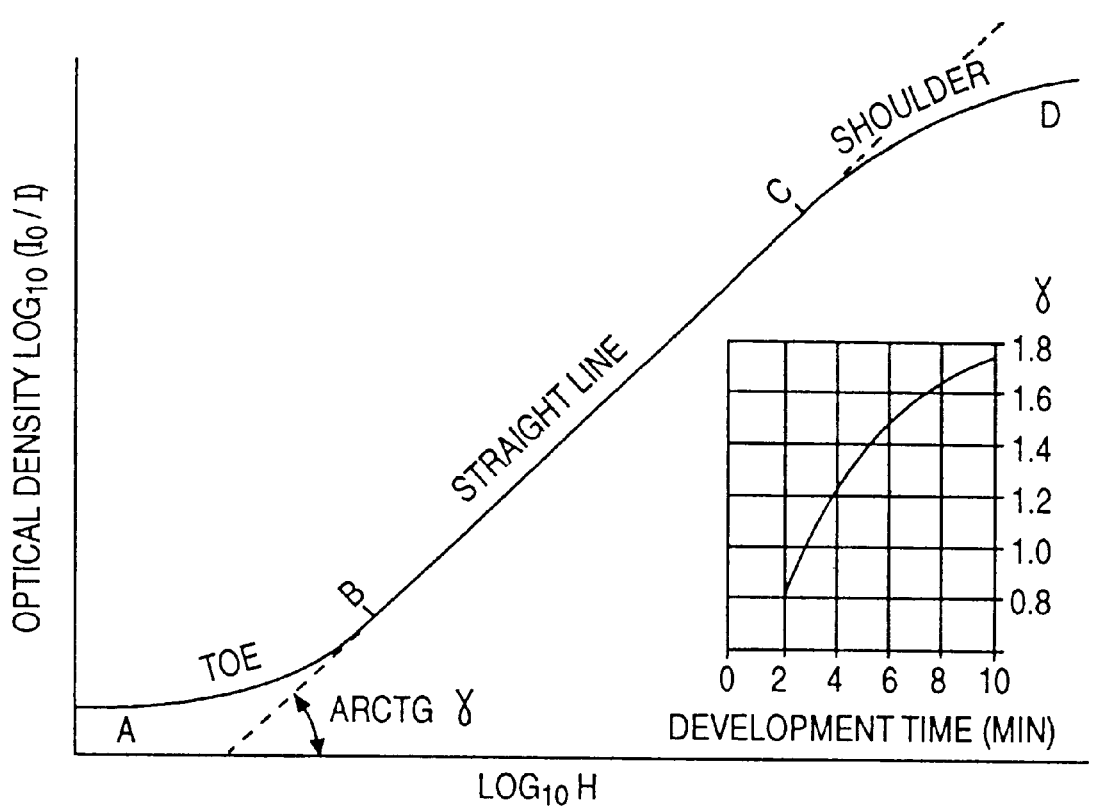
FIG. 7 is a graph showing a typical H & D curve of the optical density of the developed film versus the logarithm of the exposure H. Also shown is the "gamma" slope. The dashed straight line is the linear approximation of the H & D curve.

In Eqs. 6 and 7, $I_{0,m}$ is the pixel value associated with an unexposed but developed portion of film m; this portion of the film is known as "film base plus fog." It is to be understood that in this presently preferred embodiment of the invention, the exposure and development of the M films is assumed to occur in the linear portion of the optical density versus exposure logarithm curve (known as the "H & D curve"). Moreover, the constant γ, known as the "gamma slope" of the H & D curve, is assumed known and equal to 1. The H & D curve expresses the relationship between optical density and exposure of a developed film; a good exposition of the technical details of film exposure and development, including a discussion of the H & D curve, may be found in Chapter 20 in the book *Handbook of Optics*, Edited by Michael Bass, published by McGraw-Hill, Inc., New York, in 1995, and which is incorporated by reference hereinto. FIG. 7 provides an illustrative sketch of the H & D curve, showing its linear portion with gamma slope γ. Also shown are the "toe" and "shoulder" of the curve, as well as a curve demonstrating the effect of development time on the gamma slope, γ. It should be noted again that the weighting functions $f_m(E)$ include some effects of the film development; for example, the value of the intercept of the linearized portion of the H & D curve with the abscissa axis, as depicted in FIG. 7, is accounted for by the weighting functions.

It is to be understood that the pixel data represented by Eqs. 6 and 7 may be substituted into Eqs. 1 and 3, respectively. Eq. 1 may then be solved for the unknown weighting functions, $f_m(E)$, by discretizing the integral, namely:

$$H_{m,n,k} = \sum_{r=1}^{R} f_m(E_r) g_{n,k}^P(E_r) \Delta E_r \quad (8)$$

where the integer $\leq K \cdot Q$, and $\Delta E_r$, r=1, ..., , is an associated energy discretization. In the presently preferred embodiment, =5, and $\Delta E_r$=30 keV, 30 keV, 20 keV, 20 keV and 30 keV, for r=1,2,3,4,5, respectively. The unknown weighting functions $f_m(E_r)$ in the set of linear equations represented by Eq. 8 may be solved with a variety of computer software packages; in the presently preferred embodiment, MATLAB may again most suitably be utilized. Finally, the unknown tissue thicknesses d, =1, ..., L, may be determined by substituting the solutions for $f_m(E_r)$ into a discretized version of Eq. 3, namely:

$$T_m = \sum_{r=1}^{R} f_m(E_r) g(E_r; d_l) \Delta E_r \quad (9)$$

The solution of Eq. 3 for the tissue thicknesses d, =1, ..., L, is a nonlinear problem, which can be achieved using a variety of nonlinear optimization techniques. In the presently preferred embodiment, the solution is most suitably carried out using the Levenburg-Marquardt algorithm included with the MATLAB Optimization Toolbox software package. It is important to point out that Eqs. 8 and 9 are solved using the image pixel values in substitution for the exposure variables $H_{m,n,k}$ and $T_m$, according to Eqs. 6 and 7.

It should be understood that Eqs. 8 and 9 are obtained using standard trapezoidal approximation; however, there are a wide variety of integral discretization procedures that may be utilized. An excellent description of such numerical techniques can be found in the book by W. H. Press et al., entitled *Numerical Recipes in Fortran, The Art of Scientific Computing*, Second Edition, Cambridge University Press, 1992, and which is incorporated by reference hereinto.

In the presently preferred embodiment, and with reference to FIG. 7, it should be understood that the H & D curve is approximated by a straight line (shown for illustration purposes as a dashed line in FIG. 7), whose gamma slope is equal to one (γ=1). It should also be pointed out, however, that Eqs. 8 and 9 can be solved when γ is not assumed to be known a priori. In this alternative embodiment of the invention, the solution of Eq. 8 may most suitably be achieved through nonlinear optimization with respect to both $f_m(E_r)$ and γ. It is understood in this case that the Marquardt-Levenburg algorithm in Matlab's Optimization Toolbox may most suitably be utilized. In yet another variation of the invention, the linear as well as the nonlinear portion of the H & D curve can be used in the determination of the tissue thicknesses. In this case, it is to be understood that a parametric model of the H & D curve may be employed, and that the associated parameters of the parametric model, that is, the parameters relating to exposure and development of each film, may be identified for each film through a nonlinear optimization procedure.

It should be further understood that there can be several ways in which to obtain the M films having exposures from relatively different portions of the x-ray energy spectrum. In one such alternative embodiment of the invention, filter sheets in the energy-selective multiple-film cassette are not used; instead scintillating screens which are each responsive to relatively different regions of the x-ray beam energy spectrum are used in place of the filters and of the standard scintillating screens used supra. Such screens are well known in the art; see for example U.S. Pat. No. 4,513,078 by Sandrik et al. and U.S. Pat. No. 5,070,248 by Pesce. In another alternative embodiment, filter sheets and energy-selective scintillating screens are both used.

In certain applications, it may be useful to obtain estimates of not only bone-mineral density, but also of soft tissue density as well. It should be understood that the present invention provide an estimate of this quantity as well. Moreover, if it is desired to estimate the densities (i.e., tissue thicknesses) of more than two tissues, for example, the three tissues of bone, muscle and fat, this can also be achieved through use of the present invention. In this case, it is required to use additional phantom materials, i.e., at least three (K=3), and at least three sheets of film in the multiple-film cassette (M=3). It should also be appreciated that the use of larger numbers of films and of materials in the multiple-material phantom can be used to improve the statistical properties of the bone-mineral density and other tissue estimates. The same may be said for the use of phantoms with increased numbers of thicknesses (i.e., steps).

It should be understood that the disclosed invention can find application in several areas related to bone diagnosis. The assessment of bone-mineral density is most useful for assessing bone loss in diseases such as osteoporosis. The assessment of bone loss is important for determining the risk of fracture in elderly patients. In general, the disclosed invention should be understood to be of use for estimating the bone-mineral density of a number of anatomical sites, for example, including the hip, spine, radius, phalanges and calcaneus. The present invention can also find application to the assessment of bone-fracture healing, by allowing for more reliable evaluations of mineralization at the fracture healing site. It is also important to note that the disclosed apparatus and method may also find application in other medical fields, as well as material testing in general, not related necessarily to the medical field.

It should be additionally understood that the invention can be used with a variety of averaging, template and edge detection algorithms. These techniques are useful both for reducing noise and for isolating a specific region of interest within a given anatomical site, and allow for better reproducibility in terms of bone-mineral density estimation. It should be understood that averaging can be applied to the pixel data or exposure variables (see Eqs. 7–8), or to the estimated tissue thicknesses, d. Such averaging and region of interest techniques are well-known in the art of bone densitometry, and may be utilized in conjunction with the invention disclosed herein.

The foregoing discussion for the variations and embodiments of the invention as described in FIG. 1 has relied on a separate scanner and film processor. It will be understood however, that the respective embodiments and their variations can be implemented in radiographic systems which incorporate the processor and digital scanner directly as part of the overall plain x-ray machine. It should be further understood that a variety of types of digital scanners can be utilized in the present invention, including, for example video cameras. In general, it should be appreciated that various calibration techniques, well known in the art, may be used in conjunction with the digitization of the radiographic film, which may be applied with a digital scanner with a transparency adaptor, a video camera, or any other scanning device utilized in the present invention. It should be additionally understood that the methods disclosed herein may also be applied to computed radiology systems, which produce a direct digital radiographic image onto an imaging plate. The methods disclosed herein can be extended directly to such systems. Finally, based on the techniques disclosed herein, it should be understood that one may choose specific multiple-material phantoms (in terms of materials, number of materials and thicknesses) and specific multiple-film cassettes adapted to receive particular relative portions of x-ray source energy spectrums, in order to produce the best results possible in specific applications under particular sets of operating conditions.

It will be seen that the described invention meets all stated objectives as to evaluation of the status of bone tissue in vivo, with specific advantages that include but are not limited to the following:

(1) Implementation with standard plain x-ray radiographic equipment;

(2) Relative insensitivity of the bone-mineral density estimates to variations in overlying soft-tissue thickness;

(3) Relative insensitivity of the bone-mineral density estimates to variations in x-ray equipment, exposure settings and development;

(4) Sophisticated analysis of the data, in contrast to the prior plain radiographic absorptiometry art which relies largely on simplistic compensation techniques. In contrast, the processing described relies on rigorous x-ray radiographic principles, and employs nonlinear optimization techniques to obtain accurate and precise estimates of bone-mineral density and other tissue densities;

(5) Relatively low cost associated with the determination of bone-mineral density, which should allow for improved and expanded health care delivery to the general population.

What is claimed is:

1. A method of non-invasively and quantitatively evaluating the status of bone tissue in a bony locale of a body, as manifested through the quantity: bone-mineral density, using a collimated broadband x-ray beam, which method comprises the steps of:

(a) providing a multiple-material phantom wherein said phantom contains more than one material;

(b) providing a multiple-film cassette, wherein said cassette contains more than one film and wherein each of said films within said cassette receives different relative portions of the energy spectrum of said broadband x-ray beam;

(c) transmitting said collimated broadband x-ray beam through said bony locale of said body and through said multiple-material phantom, wherein said multiple-material phantom is placed alongside said bony locale of said body, and wherein said multiple-film cassette is positioned to receive said x-ray beam after transmission through said bony locale and said multiple-material phantom;

(d) obtaining bony locale image data and multiple-material phantom image data associated with each of said films contained within said multiple-film cassette; and (e) numerically processing said bony locale image data and said multiple-material phantom image data using a nonlinear optimization technique to evaluate said status of said bone tissue.

2. The method according to claim 1 wherein said nonlinear optimization technique comprises a Levenburg-Marquardt algorithm.

3. A method of non-invasively and quantitatively evaluating the status of bone tissue in a bony locale of a body, as manifested through the quantity: bone-mineral density, using a collimated broadband x-ray beam and a phantom, which method comprises the steps of:

(a) providing a multiple-film cassette, wherein said cassette contains more than one film and wherein each of said films within said cassette receives different relative portions of the energy spectrum of said broadband x-ray beam;

(b) transmitting said collimated broadband x-ray beam through said bony locale of said body and through said phantom, wherein said phantom is placed alongside said bony locale of said body, and wherein said multiple-film cassette is positioned to receive said x-ray beam after transmission through said bony locale and said phantom;

(c) obtaining bony locale image data and phantom image data associated with each of said films contained within said multiple-film cassette; and (d) numerically processing said bony locale image data and said phantom image data using a nonlinear optimization technique to evaluate said status of said bone tissue.

4. The method according to claim 3 wherein said nonlinear optimization technique comprises a Levenburg-Marquardt algorithm.

* * * * *